United States Patent [19]

Abraham

[11] Patent Number: 5,340,724

[45] Date of Patent: Aug. 23, 1994

[54] USE OF TAXOL-DEPENDENT CELLS TO IDENTIFY AND ISOLATE TAXOL-LIKE COMPOUNDS

[75] Inventor: Irene Abraham, Kalamazoo, Mich.

[73] Assignee: The Upjohn Company, Kalamazoo, Mich.

[21] Appl. No.: 691,326

[22] Filed: Apr. 25, 1991

[51] Int. Cl.$^5$ .................. C12Q 1/00; C12Q 1/04; C12Q 1/18; C12N 1/00
[52] U.S. Cl. .......................................... 435/32; 435/4; 435/29; 435/30; 435/240.2; 436/63; 436/64; 424/195.1
[58] Field of Search .............. 435/29, 32, 30, 4, 240.2; 436/63, 64; 424/195.1

[56] References Cited

U.S. PATENT DOCUMENTS 4,960,790  10/1990  Stella et al. .................. 514/449
5,019,504  5/1991  Christen et al. ................. 435/123

OTHER PUBLICATIONS

Parness, et al. Biochemical and Biophysical Research Communications. vol. 105, No. 3 pp. 1082–1089.
Mellado, et al. Biochemical and Biophysical Research Communications. vol. 124, No. 2, pp. 329–336.
Schibler, M. J., and Cabral F., "Taxol-dependent Mutants of Chinese Hamster Ovary Cells with Alterations in α– and β–Tubulin," J. Cell Biol., 102, pp. 1522–1531 (1986).
Cabral, et al. Annals New York Academy of Sciences pp. 745–756 vol. 466. 1986.

*Primary Examiner*—Michael G. Wityshyn
*Assistant Examiner*—Jane Williams
*Attorney, Agent, or Firm*—Debbie K. Wright; Paul J. Koivuniemi; Thomas A. Wootton

[57] ABSTRACT

The present invention relates to the use of taxol dependent cells, e.g. Tax 2-4 CHO cell line, as the basis of a screen for taxol or taxol-like compounds.

2 Claims, No Drawings

USE OF TAXOL-DEPENDENT CELLS TO IDENTIFY AND ISOLATE TAXOL-LIKE COMPOUNDS

FIELD OF INVENTION

The present invention discloses the use of taxol dependent mutant cells for screening for taxol or taxol-like compounds. More particularly, the present invention provides a method of selecting taxol or taxol-like compounds using the Tax 2-4 Chinese Hampster Ovary (CHO) cell line.

BACKGROUND OF THE INVENTION

Recent studies suggest that taxol may be an effective agent in the treatment of ovarian cancer and other tumors. These studies further suggest that taxol may be even more effective than any currently available treatment in that anti-tumor responses have also been shown in patients with cis-platinum resistant ovarian cancer (See, e.g. McGuire, W. et al, (1989) "Taxol: unique antineoplastic agent with significant activity in advanced ovarian epithelial neoplasms." Ann. Intern. Med. 111:273-279, and Rowinsky, E. et al, (1990) "Taxol: a novel investigational antimicrotuble agent." J. National Cancer Institute 82:1247-1259). Preliminary evidence also suggests that taxol is useful in the treatment of other neoplasms (See, Rowinsky supra). As a result of these findings, taxol or a drug which has a similar mode of action could have a significant and beneficial impact on cancer chemotherapy.

While the preliminary clinical results have been extremely encouraging, there are still many problems with using taxol as a therapeutic agent. At present, the most critical problem is the lack of an inexpensive and readily available source of taxol. According to published data, taxol has only been isolated from the bark or needles of *Taxus brevifolia*. These plants are extremely slow growing and the collection of bark or needles and subsequent extraction from large quantities of biological material is very labor intensive. In addition, taxol has intrinsic problems of extreme insolubility. Clinical trials suggest accompanying toxic side effects of treatment leading to neutropenia and to a lesser degree, neurotoxicity (See e.g. Rowinsky, supra). Thus while taxol is a novel chemotherapeutic of unique biological activity, research leading to alternate sources of taxol or taxol analogues would be extremely useful.

Taxol has a unique mode of action. It acts to stabilize microtubules both in vitro and in intact cells. (See Schiff, P., et al, (1979) "Promotion of microtubules assembly in vitro by taxol." Nature 227:665-667; and Schiff, P and Horwitz, S. (1980) "Taxol stabilizes microtubules in mouse fibroblast cells" Proc. Natl. Acad. Sci. USA 77:1561-1565.) While there are many known agents which stabilize or promote microtubule formation in in vitro polymerization assays, there is little evidence that any of these, aside from microtubule associated proteins and divalent cations, will stabilize microtubules in intact living cells.

Since the efficacy of taxol is presumably based on its unique mode of action of stabilizing microtubules, it seems worthwhile to look for other agents that might stabilize microtubules. To date there are no other known agents that act like taxol. While it is certainly possible that taxol is truly unique in its mode of action, it is also possible that there are other molecules, either closely related to or of distinctly different molecular structure, that might work like taxol, in terms of its ability to stabilize microtubules.

Although successful taxol synthesis appears to be possible using precursors found in abundance in the leaves of the Taxus tree, such synthesis would probably not be sufficient to meet the needs of cancer treatment each year. This has led to an intensive search for alternate sources of taxol or taxol-like compounds which stabilize microtubules. The presence of taxol or taxol-like compounds would be easier to detect if a screen were available which would rescue only such compounds. The present invention provides such a screen.

The present invention discloses the use of taxol dependent mutant cells derived from CHO cells as a screen for taxol or taxol-like compounds. This screen is based on the use of cells that die in the absence of taxol because their microtubules are intrinsically unstable due to mutations. There are several apparent advantages to such a screen. It is much more selective than a general screen for cytotoxic compounds. Another advantage of this screen, as opposed to in vitro assays, is that it is selective for only those molecules that have biological activity in intact cells. Therefore the screen of the present invention would exclude all agents that might have activity in an in vitro polymerization assay but not in an intact, viable cell. Cytotoxics without taxol-like activity would not be positively selected in this screen since they would not allow for growth of the taxol-dependent cells.

INFORMATION DISCLOSURE

Schibler, M. and Cabral, F. (1986) "Taxol-dependent mutants of Chinese hamster ovary cells with alterations in α- and β-tublin," J. Cell Biol. 102: 1522-1531, discloses taxol resistant and dependent cells. The Tax 2-4 cell line was also described by Schibler and Cabral, supra. However, this publication does not disclose the use of taxol dependent cells in general or the use of Tax 2-4 cell line in an assay as a screen for taxol or taxol-like compounds.

SUMMARY OF THE INVENTION

The present invention discloses a method of screening for taxol and taxol-like compounds comprising the steps of: contacting a potential taxol source, e.g., a plant extract, or a compound of interest with taxol dependent cells; maintaining the taxol dependent cells in contact with the source or compound for a time and under such conditions sufficient to allow cell growth; detecting cell growth and selecting a positive taxol source or taxol-like compound.

DETAILED DESCRIPTION OF THE INVENTION

The present invention allows for the convenient selection of taxol or taxol-like microtubule-stabilizing compounds by measuring viability of taxol resistant and dependent cell lines. Viability of the taxol-dependent cells can be measured in many ways, such as by sight or by the MTT assay. The MTT (3-[4,5-dimethylhiazol-2-yl]-2,5-diphenyl tetrazolium bromide) assay, which is a rapid method of detecting cellular growth, is disclosed in Mosmann, T. (1983) "Rapid colorimetric assay for cellular growth and survival: application to proliferation and cytotoxicity assays." J. Immun. Methods 65:55-63 which is incorporated herein by reference. The MTT assay is reproducible. It measures the cell toxicity, proliferation and activation with a high degree of precision. The assay as applied to the Tax 2-4 CHO cell line correlates well with cell survival and growth inhibition assays. The Tax 2-4 cells are dependent on taxol for growth (0.05-0.3 μg/ml) and are not rescued by any of the other agents tested such as puromycin, adriamycin, actinomycin D, ethidium bromide, vinblastine, bleomycin, ouabain, DMSO, glycerol, colcemid, cAMP and the phorbol ester, PMA. The taxol dose that initiates the growth of Tax 2-4 inhibits the growth of CHO (wild type). This observation may be useful as a second line of screening to confirm taxol-like activity.

By "taxol dependent cells" is meant any cell line that requires taxol or any other microtubule-stabilizing compound for growth.

By "taxol-like compounds" is meant an analog of taxol, any compound which stabilizes microtubules by a mode of action similar to taxol as evidenced by its ability to promote growth of taxol dependent cells or any compound that would promote microtubule formation in in vitro. Included in this definition are synthetic organic compounds, compounds contained in fermentation beers, plant extracts and extracts from multicellular organisms.

Taxol is a natural product compound that has been shown to act by stabilizing microtubules in vitro and in vivo. The screen of this invention is based on measuring the viability of taxol dependent cells grown in tissue culture conditions. These cells will die unless supplied with taxol or other microtubule-stabilizing compounds. Therefore, any molecule or extract that allows the viability of these cells will most likely have taxol or taxol-like microtubule stabilizing activity. The present invention can be used to test for previously identified compounds, new compounds, compounds in fermentation broth extracts, plant extracts or extracts from multicellular organisms that will allow these cells to survive. Only those taxol-like materials that act to stabilize the microtubules in a manner analogous to taxol, will be able to substitute for taxol in this assay.

Since these taxol dependent cells will only grow if taxol or a taxol-like substance is present in the media, potential taxol analogues, e.g., molecules that would stabilize intercellular microtubules, will thus be selected. Alternate sources of taxol could also be identified. Development of such a drug screen will allow the specific and direct testing for intracellularly active microtubule stabilizers. This is the only screen design that would allow the screening of large numbers of potential stabilizing compounds or extracts in a relatively short time. An important advantage of this screen, as opposed to an in vitro tubulin polymerization screen, is that this screen will only detect agents able to enter the cell and having intracellular activity.

The present invention discloses the use of taxol dependent Chinese Hamster Ovary (CHO) cell lines, in an assay as a screen for taxol and taxol-like compounds. Such taxol-dependent CHO cells are described in Schibler, M. and Cabral, F. (1986) "Taxol-dependent routants of Chinese hamster ovary cells with alterations in α- and β-tublin." J. Cell Biol. 102: 1522-1531 which is incorporated herein by reference. It is contemplated that any of the taxol-dependent cell lines which can be made according to Schibler and Cabral can be used in the instant invention. More particularly, the present invention discloses the use of Tax 2-4 CHO cell line (Dr. F. Caleral, University of Texas, Houston) or an equivalent cell line in an assay as a screen for taxol and taxol-like compounds. The Tax 2-4 cell line is also described in Schibler and Cabral, supra. Growth of Tax 2-4 depends upon the presence of taxol which cannot be replaced by other agents. The growth of Tax 2-4 increases with increasing taxol concentration up to 0.05 μg/ml. Optimum growth occurs between 0.05-0.3 μg/ml and at higher doses, taxol inhibits the growth of Tax 2-4.

Based upon Examples 2 and 3, the following protocol is suggested. Taxol-dependent cells are added at $2.4 \times 10^3$/well or $10^3$/well to allow logarithmic growth during 3 or 4 days of assay incubation. The acetone extract of a fermentation broth which is dried and then dissolved in DMSO (dimethyl sulfoxide) is tested. The DMSO solution is diluted to 1:200 in order to reduce the DMSO concentration to 0.5%. The extract is tested at 3 concentrations, the highest dose, 1:2 and 1:4 dilutions of that dose. After 3 or 4 days incubation, taxol-dependent cell growth is determined by the MTT assay.

The present invention is seen more fully by the examples set forth below.

EXAMPLE 1

Sensitivity of Various Strains to Taxol

This example shows that Tax 2-4 is the best choice of currently available cells for a high volume screen for taxol-like acting agents and that the wildtype and taxol resistant cell lines would be good cells lines to use either concurrently or as a secondary screen to confirm the identification of taxol-like agents. The results suggest that Tax 2-4 would show growth in taxol or taxol-like agents over a 150 fold range in concentration. At lower and higher concentrations the cells will die. Thus, log or half-log dilutions of fermentation beers or other compounds with taxol-like activity would be detectable with this cell line. It is expected that concentrations of the unknowns that optimally stimulate growth of the Tax 2-4 cells would cause about 50% lethality in the wildtype cells and resistance in the 10576 cell lines (Cabral, F. et al, (1981) "Isolation of a taxol resistant Chinese hamster ovary cell mutant that has an alteration in α-tubulin." Proc. Natl. Acad. Sci. 78:4388-4391.)

Two Chinese Hamster Ovary (CHO) cell lines, Tax 2-4 (Schibler and Cabral et al, (1986) J. Cell. Biol. 102: 1522-1531) and Tax 18 (Cabral, et al. (1983) J. Cell. Biol. 97:30-39, were tested for sensitivity to taxol (Natural Products Branch, NIH) as well as to colecimid (Sigma), cAMP (Sigma) and the phorbol ester, PMA (Sigma). Results showed that only the Tax 2-4 strain was absolutely dependent upon taxol and was not rescued by any other drugs tested. Thus, the tax 2-4 cell line is the most suitable for use in a screen for taxol-like analogs. The growth of Tax 18, while being dependent on taxol, is also promoted by the presence of PMA, thus making it unsuitable for a screen for taxol-like agents.

The viability of other CHO cell lines was also studied. These cell lines were a wildtype, 10001 (American Type Culture Collection CCL 61); a colcemid resistant mutant, 10193 (Cabral, et al. (1980) Cell 20:29-36); a colcemid dependent mutant, 11801 (Whitfield et al., (1986) Mol. Cell. Biol. 6:1422-1429); and a taxol resistant mutant, 10576 (Cabral, et al. (1980) Cell 20:29-36). The data showed that taxol will cause the growth of Tax 2-4 at doses that would be lethal to 10001, 10193, or 11801 cells. Tax 2-4 and Tax 18 are viable at a level that kills over 33% of the wildtype cells. The drug concentration for Tax 2-4 and Tax 18 at which half of the cells die ($IC_{50}$) was determined. Tax 2-4 and Tax 18 cells have an $IC_{50}$ that is 8.3 and 4.7-fold higher, respectfully, than that of wildtype cells. The 11801 colcemid dependent cells are more sensitive to taxol than the wildtype cells. Tax 2-4 and Tax 18 have an $IC_{50}$ over 40-fold and 80-fold respectively, higher than 11801. The colcemid resistant line, 10193, while reported to have been more sensitive to taxol than wildtype, showed no difference in sensitivity as compared to the wildtype. The taxol-resistant line 10576 was not as resistant to taxol as either the Tax 2-4 or Tax 18 cells.

EXAMPLE 2

Use of Tax 2-4 CHO cell line with the MTT assay as a screen for taxol-like compounds Tax 2-4 cells are plated at $10^3$ cells per well of a 96 well culture dish according to standard procedures. Test material is added to each well and cells are allowed to grow for 4 days. Control cells are also grown in the presence of 0.001 to 1.0 µg/ml taxol to verify the authentic taxol dependency of the cells and to provide a standard curve for survival. After 4 days, MTT solution is added to wells and the cells are incubated for 3 hours as described (Mossmann, J., Immun. Methods 65:55–63 (1983)). This solution is removed from the cells and the cells are dissolved in isoproponal. The plates are shaken and resulting color, indicating viability, is quantitated by reading on a microplate reader. Test compounds that give reading equivalent to that achieved by 0.004 µg/ml taxol in the control plates are considered positive.

Several extracts prepared from Taxus sp. plants (Dr. C. J. Chang at Purdue University and Dr. P. Chee, Upjohn) were tested. Methanol extracts of these plants caused increased viability of the Tax 2-4, indicating the presence of taxol or taxol-like analogs.

EXAMPLE 3

Use of Tax 2-4 CHO cell line with methylene blue colony forming assay as a screen for taxol like compounds 200 Cells per well are plated in 24 well dishes. Test material is added to each well and cells are allowed to grow for 7 days. Control cells are also grown in the presence of varying concentrations of taxol (0.001 to 1.0 µg/ml) to verify the taxol dependency of the cells, and provide a standard curve for survival in taxol. After 7 days, the media is removed and the cells are stained in 0.5% methylene blue in ethanol. After 15 min any stain is removed, plates are rinsed in water and the colonies (consisting of greater than 50 cells) are counted. The presence of greater than 3 colonies per well is considered positive for the presence of taxol or taxol-like compounds.

I claim:

1. A method of screening for taxol-like materials that act to stabilize microtubules in a manner analogous to taxol comprising the steps of:
   a) contacting the taxol-like materials with taxol dependent cells:
   b) maintaining the taxol dependent cells in contact with the taxol-like materials for a time and under such conditions sufficient to allow cell growth;
   c) detecting cell growth; and
   d) selecting compounds that allow such growth.

2. A method according to claim 1 wherein the taxol-dependent cells are Tax 2-4.

* * * * *